(12) United States Patent
Dettloff et al.

(10) Patent No.: US 6,482,946 B1
(45) Date of Patent: Nov. 19, 2002

(54) HIGH CHAR YIELD BENZOXAZINE COMPOSITIONS

(75) Inventors: Marvin L. Dettloff, Lake Jackson, TX (US); Jerry E. White, Lake Jackson, TX (US); Marty J. Null, Lake Jackson, TX (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 09/705,685

(22) Filed: Nov. 3, 2000

Related U.S. Application Data

(60) Provisional application No. 60/163,829, filed on Nov. 5, 1999.

(51) Int. Cl.$^7$ .............................................. C07D 265/16
(52) U.S. Cl. ....................... 544/73; 528/129; 528/137; 528/145; 528/146; 528/150; 528/408; 544/69; 544/90
(58) Field of Search .............................. 544/73, 90, 96, 544/69; 528/129, 154, 408, 137, 145, 146

(56) References Cited

U.S. PATENT DOCUMENTS

| | | | |
|---|---|---|---|
| 2,098,869 A | 11/1937 | Harmon et al. | ................. 260/4 |
| 5,152,939 A | 10/1992 | Ishida | ......................... 264/291 |
| 5,543,516 A | 8/1996 | Ishida | ......................... 544/69 |
| 5,973,144 A | * 10/1999 | Ishida | ......................... 544/73 |

FOREIGN PATENT DOCUMENTS

| | | |
|---|---|---|
| CH | 606 169 | 10/1978 |
| EP | 0 789 056 A2 | 8/1997 |
| JP | 8-74896 | 3/1996 |
| JP | 9-59333 | 3/1997 |
| WO | WO 89/05803 | 6/1989 |
| WO | WO 99/18092 | 4/1999 |
| WO | WO 00/61650 | 10/2000 |

OTHER PUBLICATIONS

Engle, et al., "A Review of Thermally Controlled Covalent Bond Formation in Polymer Chemistry," Rev. Macromol. Chem. Phys., C33(3), pp. 239–257 (1993).

Brunovska, et al., "Thermal Study on the Copolymers of Phthalonitrile and Phenylnitrile–Functional Benzoxazines," Journal of Applied Polymer Science, vol. 73, pp. 2937–2949 (1999).

Low, et al., "Structural effects of phenols on the thermal and thermo–oxidative degradation of polybenzoxazines," Polymer, vol. 40, pp. 4365–4376 (1999).

Low, et al., "An Investigation of the Thermal and Thermo–Oxidative Degradation of Polybenzoxazines with a Reactive Functional Group," Journal of Polymer Science Part B: Polymer Physics, vol. 37, pp. 647–659 (1999).

Laita, et al., "The Application of the Diels–Alder Reaction to Polymers Bearing Furan Moieties. 1. Reactions with Maleimides," Eur. Polym. J., vol. 33, No. 8, pp. 1203–1211 (1997).

Ruping, et al., "Investigation on Ring–opening Polymerized Phenolic Resin Automatic Brake Materials," Journal of Chengdu University of Science and Technology, vol. 95, pp. 64–70 (1996).

Goussé, et al., "Diels–Alder polymerization of difurans with bismaleimides," Polymer International, vol. 48, pp. 723–731 (1999).

Goussé, et al., "Application of the Diels–Alder Reaction to Polymers Bearing Furan Moieties. 2. Diels–Alder and Retro–Diels–Alder Reactions Involving Furan Rings in Some Styrene Copolymers," Macromolecules, vol. 31, pp. 314–321 (1998).

Hui, et al., "Polymeric Schiff Bases Bearing Furan Moieties," Eur. Polym. J., vol. 28, pp. 1461–1469 (1992).

Ishida, "Development of Polybenzoxazines: A New Class of High Performance, Ring–Opening Phenolic Resins with Superb Balance of Physical and Mechanical Properties," Mark./Tech./Regul. Sess. Compos. Inst. Int. Expo. '98, pp. 14B/1–14B/8 (1998).

Kim, et al., "Molecular characterization of the polymerization of acetylene–functional benzoxazine resins," Polymer 40, pp. 1815–1822 (1998).

\* cited by examiner

Primary Examiner—Richard L. Raymond
(74) Attorney, Agent, or Firm—Kevin J Nilsen

(57) ABSTRACT

A high char yield polybenzoxazine is formed by mixing (i) a benzoxazine compound, (ii) a furan compound, (iii) a benzoxazine-furan compound or combinations thereof, wherein the mixture has a benzoxazine ring to furan ring ratio from about 0.001 to about 10 and then heating the mixture for a sufficient time to form the polybenzoxazine.

38 Claims, No Drawings

HIGH CHAR YIELD BENZOXAZINE COMPOSITIONS

CROSS-REFERENCE TO RELATED APPLICATION

This application claims the benefit of U.S. Provisional Application Serial No. 60/163,829 filed Nov. 5, 1999.

FIELD OF THE INVENTION

The invention relates to benzoxazines, high char yield polybenzoxazines formed therefrom and method of forming said polybenzoxazines.

BACKGROUND OF THE INVENTION

Benzoxazines are a class of phenolic resins that are generally formed by the reaction of a phenol, primary amine and formaldehyde or paraformaldehyde. The benzoxazine may be polymerized by simple heating to open the oxazine ring. This leads to the formation of a chemical bond between the phenolic groups. Cross-linked (i.e., thermoset) polybenzoxazines generally require multi-functional benzoxazine monomers (i.e., they contain more than two reactive sites). Generally, cross-linked polybenzoxazines are formed from benzoxazine monomers having more than one benzoxazine rings.

Benzoxazines exhibit several advantages for forming thermally stable polymers compared to resole phenolics and novolacs. For example, benzoxazines do not form any volatile reaction products upon polymerization, which is, for example, an advantage for forming composite parts (i.e., no out-gassing). In addition, they do not require the use of strong acid polymerization catalysts; such as used to cure resoles, which can cause corrosion of a mold.

One of the desirable traits of the cured benzoxazines is their potential to achieve high char yields, which are indicative of their thermal stability. However, many of the benzoxazine monomers that give cured products with high char yields often have limited processability because of their high viscosity below their reaction temperature. This makes them more suitable for processing methods, such as compression molding, rather than high speed processing methods, such as pultrusion. That is to say, they do not achieve desirable processing viscosities (i.e., sufficient to easily impregnate fiber matrices) without the aid of a solvent or substantial heating.

Unfortunately, the use of a solvent adds processing steps to remove it. The disadvantage of applying heat to the neat resin (benzoxazine) is that at the temperatures (e.g., about 160° C.) needed to achieve a reasonable processing viscosity (e.g., <1000 centipoise) the benzoxazines autopolymerize resulting in a very short processing time. As a result, the viscosity builds faster than the ability to efficiently impregnate the fiber mat because of polymerization. Consequently, a method of obtaining both high char yields and good processability, without the use of solvents, is desirable for extending the utility of benzoxazines into applications, such as structural composites.

A recent attempt to increase the char yield of polybenzoxazines has been described by Ishida in WO 99/18092. Ishida describes incorporating a pendant reactive group, either to the phenolic or amine reactants, to create the benzoxazine monomer. The pendant reactive group is a group that is reactive with itself (e.g., acetylene group) or is a first reactive pendant group that is reactive with a second pendant reactive group, neither being reactive with itself. Unfortunately, even though these benzoxazines are reported to increase the char yield, they fail to address the processing problems described above.

Accordingly, it would be desirable to provide a polybenzoxazine that overcomes one or more of the problems of the prior art, such as one of those described above. It would be particularly desirable to provide an easily processed benzoxazine composition that still forms a high char yield polybenzoxazine.

SUMMARY OF THE INVENTION

A first aspect of the present invention is a polybenzoxazine comprised of the reaction product of a mixture comprised of (i) a benzoxazine compound, (ii) a furan compound, (iii) a benzoxazine-furan compound or (iv) combinations thereof, wherein the mixture has a furan ring to benzoxazine ring ratio of at least about 0.001 to at most about 10.

A second aspect of the invention is a method of forming a polybenzoxazine comprised of:

mixing (i) a benzoxazine compound, (ii) a furan compound, (iii) a benzoxazine-furan compound or (iv) combinations thereof, wherein the mixture has a furan ring to benzoxazine ring ratio of at least about 0.001 to at most about 10 and heating the mixture for a sufficient time to form the polybenzoxazine.

A third aspect is a mixture useful for preparing a polybenzoxazine comprised of (i) a benzoxazine compound, (ii) a furan compound, (iii) a benzoxazine-furan compound or (iv) combinations thereof, wherein the mixture has a furan ring to benzoxazine ring ratio of at least about 0.001 to at most about 10.

In the broadest sense, the benzoxazine compound is a compound that contains at least one benzoxazine ring, but fails to have a furan ring. Similarly, the furan compound is a compound that contains at least one furan ring but fails to have a benzoxazine ring. Finally, the benzoxazine-furan compound contains at least one furan ring and at least one benzoxazine ring. Practically, each of the compounds, generally, has at most about 100 carbon atoms.

Surprisingly and unknown until the present invention, it has been discovered that a furan group, which does not react with itself, can be combined with a benzoxazine to give polymers with improved char yields after curing. Furthermore, it is unnecessary and may even be detrimental to add a compound containing a group that is reactive with the furan (i.e, maleimide) to the benzoxazine compound or benzoxazine-furan compound to obtain increased char yield. That is to say, the mixture preferably fails to have a benzoxazine compound that contains a maleimide group when the benzoxazine-furan compound is present in the mixture. It is even more preferable to have the mixture devoid of any maleimide.

In addition, the invention allows, for example, the use of certain benzoxazine-furan compounds that have only one benzoxazine ring and one furan group to unexpectedly form a thermoset polymer by itself. This type of compound also has been found to reduce the viscosity of a benzoxazine compound or benzoxazine-furan compound containing more than one benzoxazine ring without being detrimental to the final properties, such as char of the resultant polybenzoxazine.

These new polybenzoxazines may be used in the same applications as polymers, such as polyimide, phenolics, epoxies and other thermally stable polymers. In particular, they may be used in applications that take advantage of properties, such as fire resistance and low water absorption. Examples of applications include brake pads or composite applications, such as interiors and structural components of an aircraft, piping, ladders, ship masts, gratings, table trays, ducts, beams, ship housings, and printed wiring boards.

DETAILED DESCRIPTION OF THE INVENTION

The polybenzoxazine is comprised of the reaction product of a mixture comprised of (i) a benzoxazine compound, (ii) a furan compound, (iii) a benzoxazine-furan compound or (iv) combinations thereof, wherein the mixture has a furan ring to benzoxazine ring ratio of at least about 0.001 to at most about 10.

Because of the furan ring to benzoxazine ring ratio limitation, it is understood that the mixture must contain at least some amount of either the furan compound or benzoxazine-furan compound. That is to say, one of these has to be present in the mixture to provide the furan ring required by the furan/benzoxazine ring ratio. The mixture preferably contains the benzoxazine compound and the furan compound. In addition, it is preferred to have a benzoxazine compound or benzoxazine-furan compound that has more than one benzoxazine ring in the mixture. More preferably, the mixture contains a benzoxazine-furan compound that has at least two benzoxazine rings and at least one furan ring. Even more preferably, the mixture contains a benzoxazine-furan compound having at least two benzoxazine rings, in combination with a benzoxazine-furan compound that has one benzoxazine ring and one or more furan rings.

To reiterate, the ratio of furan to benzoxazine rings in the mixture is at least about 0.001 to at most about 10. Preferably, the ratio is at least about 0.1, more preferably at least about 0.2, even more preferably at least about 0.4 and most preferably at least about 0.5 to preferably at most about 8, more preferably at most about 7, even more preferably at most about 5 and most preferably at most about 4.

The benzoxazine compound may be any suitable benzoxazine, such as those known in the art. The benzoxazine may be, for example, those described by U.S. Pat. No. 5,543,516; WO 99/18092 and Japanese Patent Application HEI 9-59333.

Preferred benzoxazine compounds include those of the formula:

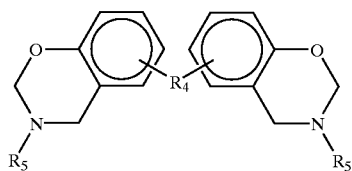

where $R_4$ is a divalent radical that is (a) an aliphatic, aromatic or combination thereof and composed of 1–35 carbon atoms, together with up to five atoms selected from the group consisting of oxygen, nitrogen, sulfur, phosphorous, halogen and combinations thereof; (b) a single bond or (c) S, $S_2$, SO, $SO_2$, O or CO and $R_5$ is one or more H, substituted or unsubstituted alkyl of 1 to 24 carbon atoms, or aromatic or substituted aromatic or aromatic substituted alkyl of 6 to 24 carbon atoms. Preferably, $R_4$ is a single carbon that has bonded to it one or more groups, such as H, $CH_3$, $C_2H_5$, $C_3H_7$, n-$C_3H_7$, i-$C_3H_7$, cyclohexyl, bicyclohexyl(2.2.1)heptyl, phenyl, $CF_2$, $CF_3$, $CCl_3$, $CF_2Cl$, CN, $(CH_2)_2COOH_3$ or $PO(OCH_3)_2$. More preferably, $R_4$ is one carbon directly bonded to two $CH_3$ groups or two hydrogens. Preferably, $R_5$ is an unsubstituted alkyl of 1 to 24 carbon atoms or unsubstituted aryl of 6 to 24 carbon atoms. More preferably, $R_5$ is a 6 to 12 unsubstituted aryl. Most preferably, $R_5$ is a phenyl.

$R_5$ may also contain at least one reactive group described previously. The reactive group may be, other than a furan group, a group such as an alkene (i.e., C=C), alkyne (i.e., C≡C), nitrile (i.e, C≡N), oxazole, oxazoline, phenol, epoxy, anhydride or imide. Examples of preferred $R_5$ structures are:

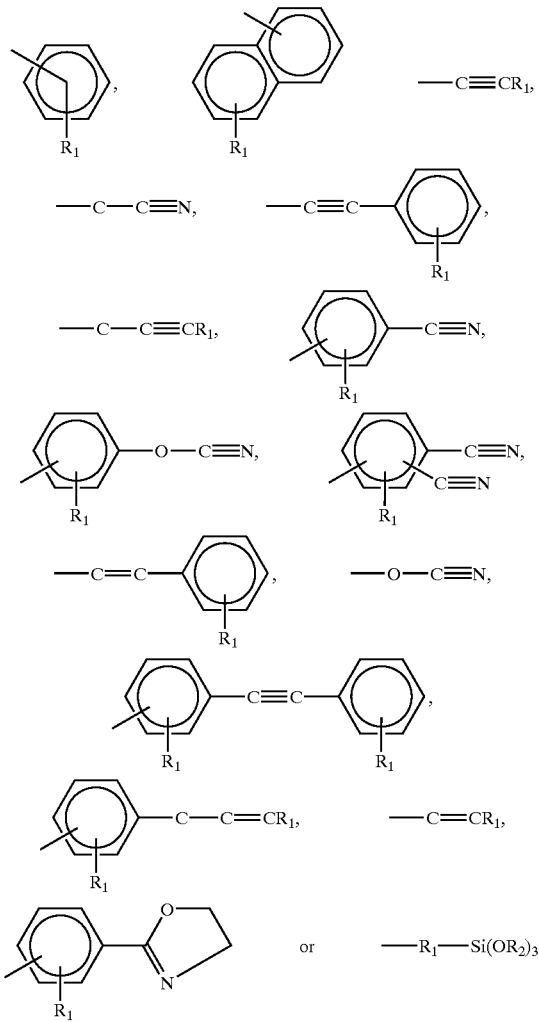

where $R_1$ is one or more H, halogen, substituted or unsubstituted alkyl of 1 to 6 carbon atoms, or aromatic or substituted aromatic (e.g., a benzoxazine, but not a furan) or aromatic substituted alkyl of 6 to 24 carbon atoms and $R_2$ is an alkyl of 1 to 5 carbon atoms, a halogen, a phenyl or combinations thereof. $R_1$ may be a cyclic, linear or branched alkyl. $R_1$ may be substituted with a group containing 1–3 atoms of O, N, P, S, halogen or combinations thereof. Preferably, $R_1$ is H, OH, a substituted aromatic or aromatic substituted alkyl of 6 to 18 carbon atoms, more preferably of 6 to 12 carbon atoms. More preferably, $R_1$ is H, OH, unsubstituted or substituted alkyl having 1 to 6 carbons. Most preferably, $R_1$ is H or OH.

Generally, the furan compound is given by the formula:

wherein X is composed of a total of 1–50 carbon atoms and up to 10 atoms selected from the group consisting of oxygen, nitrogen, sulfur, phosphorous, halogen and combinations thereof. Preferably, X is composed of at most about 30, more preferably at most about 25, even more preferably at most about 20, and most preferably at most about 18 carbon atoms. Preferably, X contains at most about 9, more preferably at most about 8, even more preferably at most about 7 and most preferably at most about 6 atoms selected from the group consisting of oxygen, nitrogen, sulfur, phosphorous, halogen and combinations thereof.

Preferably X contains a reactive group. The reactive group is a group that reacts with either another reactive group (e.g., an alkene reacting with another alkene) other than the furan or with the benzoxazine of the benzoxazine compound. Thus, a furan ring is believed to be a reactive group and is treated as such herein because of the belief that it reacts with the benzoxazine ring. The other reactive group may be another furan group or may be a group, such as an alkene (i.e., C=C), alkyne (i.e., C≡C), nitrile (i.e, C≡N), oxazole, oxazoline, phenol, epoxy, anhydride and imide. Reactive group examples, besides the furan, include:

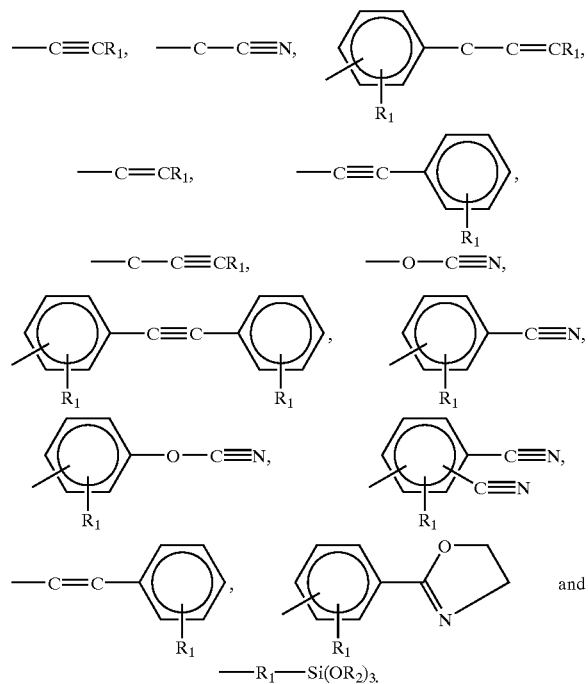

where $R_1$ and $R_2$ are the same as described above.

Preferred furan compounds include (1) compounds of a reaction between an aldehyde or ketone-containing furan group with a primary amine (i.e., Schiff base), such as those described by Hui, et al., *Eur. Polym. J.*, Vol., 28, No. 12, 1461–1469 (1992); (2) hydrogenated Schiff bases described by (1); (3) compounds of a reaction between a polyol (e.g., diol and triol) and an aldehyde containing a furan (e.g., furfural) to form, for example, an acetal, such as those described by Gousse, et al., *Polymer International*, Vol. 48, 723–741 (1999); (4) a polymer containing a furan described by Laita, et al., *Eur. Polym. J.*, Vol. 8, 1203–1211 (1997) and (5) Gousse, et al., *Macromolecule*, Vol. 31, 314–321 (1998).

To reiterate, the benzoxazine-furan compound has at least one benzoxazine ring and at least one furan, such as those shown in the formula:

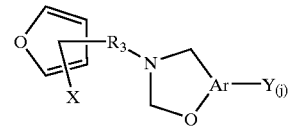

wherein X is as described previously, Ar is a benzene ring or 2 to 4 fused benzene rings, j is an integer from 4–10 and Y is independently a monovalent radical that is H; OH; halogen (e.g., fluorine, bromine, chlorine) or an alkyl, aryl, alkenyl, alkynyl or combination thereof composed of 1–35 carbon atoms containing up to 5 atoms selected from the group consisting of oxygen, nitrogen, sulfur, phosphorous, halogen and combinations thereof.

Although Ar may be a benzene ring, or 2 to 4 fused benzene rings, Ar is preferably the benzene ring or 2 fused benzene rings (i.e., naphthalene-type structure). Most preferably, Ar is a benzene ring.

When Y is an alkyl, aryl, alkenyl and alkynyl or combination thereof, Y preferably contains at most about 24, more preferably at most about 18 and most preferably at most about 12 carbon atoms. It is also understood that this monovalent radical may have combinations of alkyl, aryl, alkenyl and alkynyl (i.e., saturated, unsaturated and aromatic double bonds). Y may also be cyclic, linear or branched. When Y has an aryl constituent, the aryl may be heteroaromatic, such as aromatic compounds containing, for example, O, S, N or combinations thereof. That is to say, Y may contain a benzoxazine and furan group.

Preferred benzoxazine-furan compounds include those with the formulas:

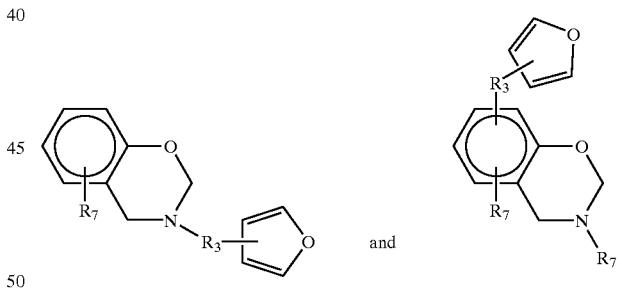

where $R_3$ is a single bond or substituted or unsubstituted alkyl group having from 1–6 carbon atoms and $R_7$ is one or more H, halogen, substituted or unsubstituted alkyl of 1 to 24 carbon atoms, or aromatic or substituted aromatic (e.g., contains a benzoxazine or furan group) or aromatic substituted alkyl of 6 to 24 carbon atoms. $R_7$ may be a cyclic, linear or branched alkyl. $R_7$ may be a group containing 1–12 atoms of O, N, P, S, halogen or combinations thereof. Preferably, $R_7$ is H, a substituted aromatic or aromatic substituted alkyl of 6 to 24 carbon atoms, more preferably of 6 to 12 carbon atoms. More preferably, $R_7$ is H, an unsubstituted or substituted alkyl having 1 to 6 carbons. Most preferably, $R_7$ is H or an unsubstituted alkyl having 1 to 6 carbons. Preferably, $R_3$ is a $C_1$ to $C_6$ unsubstituted alkyl. More preferably, $R_3$ is $CH_2$ or $C_2H_4$. Most preferably, $R_3$ is $CH_2$.

More preferred benzoxazine-furan compounds include compounds having the following formulas:

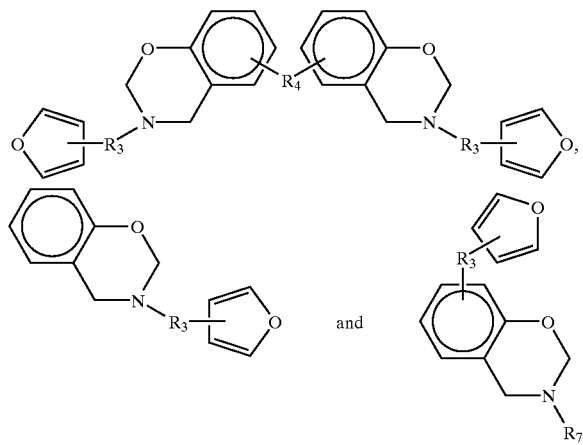

and where $R_3$ and $R_4$ are as described previously and $R_7$ is as described previously, with the proviso that it is devoid of a benzoxazine and furan group.

Preferred benzoxazine-furan compounds containing one benzoxazine and one furan (i.e., $R_7$ lacks a benzoxazine and furan group and the benzoxazine-furan compound is not of an unsubstituted phenol) have surprisingly been found to not only form a thermoset cross-linked polymer, but also reduce the viscosity, particularly at temperatures below the temperature of polymerization, of a benzoxazine or benzoxazine-furan compound having at least two benzoxazine rings without being detrimental to properties, such as char yield. Even more surprising is that the addition of these to a benzoxazine or benzoxazine-furan compound containing more than one benzoxazine ring improves properties, such as char yield (i.e., increase char yield) of the resultant polybenzoxazine. These improvements are more readily observed when the addition is to the benzoxazine compound having more than one benzoxazine ring.

Generally, the benzoxazine or benzoxazine-furan compound is made by reacting a phenol, primary amine and formaldehyde or paraformaldehyde. Examples of phenols suitable in making the benzoxazine include those having the formula:

wherein Ar is a benzene ring or 2 to 4 fused benzene rings and l is an integer from 6–12 and Y is independently a monovalent radical that is H; OH; halogen (e.g., fluorine, bromine, chlorine) or an alkyl, aryl, alkenyl, alkynyl, or combination thereof, composed of 1–35 carbon atoms containing up to 5 atoms selected from the group consisting of oxygen, nitrogen, sulfur, phosphorous, halogen and combinations thereof, with the proviso that at least one Y is OH that has an H ortho thereto.

Although Ar may be a benzene ring or 2 to 4 fused benzene rings, Ar is preferably the benzene ring or 2 fused benzene rings (i.e., naphthalene type structure). Most preferably, the Ar is a benzene ring.

When Y is an alkyl, aryl, alkenyl and alkynyl or combination thereof, the radical preferably contains at most about 24, more preferably at most about 18 and most preferably at most about 12 carbon atoms. It is also understood that this monovalent radical may have combinations of alkyl, aryl, alkenyl and alkynyl (i.e., saturated, unsaturated and aromatic double bonds). Y may also be cyclic, linear or branched. When Y has an aryl constituent, the aryl may be heteroaromatic, such as aromatic compounds containing, for example, O, S, N or combinations thereof.

Examples of monovalent Y radicals include reactive groups described previously. Preferably, Y is H, OH or an alkyl of at most about 6 carbons. More preferably, Y, other than the one required OH, is H.

Preferred phenolic compounds have the formulas:

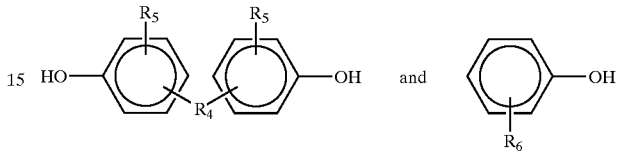

where $R_4$ and $R_5$ are the same as previously defined. Examples of phenols include phenol; cresol; 2-bromo-4-methylphenol; 2 allylphenol; 1,4-aminophenol; phenolphthalein; 2,2'-biphenyl; 4,4'-methylene-diphenol; 4,4'-dihydroxybenzophenone; bisphenol A; 1,8-dihydroxyanthraquinone; 1,6-dihydroxnaphthalene; 2,2'-dihydroxyazobenzene; resorcinol; fluorene bisphenol; 1,3, 5-trihydroxy benzene; novolac resin and polyvinyl phenol.

The primary amine may be any suitable amine to react with the phenolic compound, such as those known in the art. It is preferred that a reactive group, such as those described above, is bonded to the nitrogen. More preferably, the primary amine has the formula:

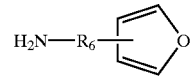

where $R_6$ is a single bond or a divalent alkyl radical having from 1 to 6 carbon atoms. Preferably, the primary amine is furfurylamine.

Other examples of amines include monofunctional amines (i.e., one amine) and include those with up to 40 carbon atoms, such as ammonia; methylamine; 5-methylfurfurylamine; ethylamine; propylamine; butylamine; isopropylamine; octadecylamine; cyclohexylamine; alkylamine; 1 aminoanthracene; 4-aminobenzaldehyde; 4-aminobenzophenone; aminobiphenyl; 2-amino-5-bromopyridine; 3-amino-ε-caprolactam; 2-amino-2,6-dimethylpiperidine; 3-amino-9-ethylcarbazole; 4-(2-aminoethyl)morpholine; 2-aminofluorenone; 2-aminofluorene; 1-aminohomopiperidine; 9-aminophenanthrene; 1-aminopyrene; 4-bromoaniline and aniline.

Examples of multifunctional amines (i.e., more than one amine) include those having up to 40 carbon atoms, such as 2-aminobenzylamine; 1,3-diaminopropane; 1,4-diaminobutane; 1,10-diaminodecane, 2,7-diaminofluorene; 1,4-diaminocyclohexane; 9,10-diaminophenanthrene; 1,4-diaminopiperizine; 4,4'-methylenedianiline; 4,4'-diaminobenzophenone; diaminodiphenylsulfone; diaminodiphenylsulfide; 4,4'-oxydianiline; melamine; fluorenetetraamine and tetraaminediphenylether.

The benzoxazine or benzoxazine-furan compound may be made by any suitable method, such as those known in the art. Exemplary methods include those described by U.S. Pat. Nos. 5,543,516 and 5,152,939; WO 99/18092; Japanese Patent Application Nos. Hei 9-59333 and Hei 8-74896 and Swiss Patent A5 11 606169. Generally, the benzoxazine is made by reacting a phenolic compound, such as those described above with a primary amine and formaldehyde, paraformaldehyde or combination thereof in an equivalent ratio of phenol, amine and aldehyde of about 1:1:2. Variations from this equivalent ratio may be used such as those described by Swiss Patent A5 11 606169.

In making the benzoxazine, a phenol, primary amine and formaldehyde or paraformaldehyde are combined with or without a solvent. This mixture is then heated to a temperature sufficient to form the benzoxazine. Generally, the temperature is from about 70° C. to about 100° C. Preferably, the temperature is at least about 80° C. After cooling, if a solvent is used, it may be removed by any suitable method, such as those known in the art. Examples of suitable solvents are dioxane, toluene, n-butyl acetate and methylisobutyl ketone.

The polybenzoxazine is generally made by heating the mixture compound to a temperature for a time sufficient to form the polybenzoxazine. The temperature is desirably at least about 70° C. to at most about 300° C. Preferably, the temperature is at least about 100° C. and more preferably at least about 150° C. to preferably at most about 250° C. and more preferably at most about 225° C. Generally, the time at temperature to form the polybenzoxazine is from about 1 minute to about 20 hours.

Polymerization of the benzoxazines is usually done without the use of a solvent, however, a solvent may be used, for example, to facilitate application of the monomer to a substrate. Examples of solvents that may be used include dioxane, tetrahydrofuran, acetone, dimethylformamide, toluene, n-butyl acetate and methylisobutyl ketone.

Even though a catalyst is not necessary, one may be used. Typical catalysts are described in *J. Appl. Polym. Sci.*, 1995, 58, 1751–1760; *J. Polym. Sci, Part A: Polym. Chem.*, 1999, 37, 1913–1921; *Polymer*, 1999, 40, 4563–4570; *Poly. Mat. Sci. Eng.*, 1999, 81, 114–115 and GB 1 437 814 and include compounds, such as acids, phenols, novolacs, Lewis acids and bases. When a catalyst or initiator is used, it is employed in small quantities, such as 0.01 percent to about 5 percent by weight of the mixture.

When forming the polybenzoxazine, another additive may also be added for reasons, such as color, fire retardancy, mechanical properties, processing properties and electrical properties. An example of an additive is an epoxy resin, such as those known in the art.

EXAMPLES

Analytical Measurement Techniques
Viscosity Measurements

Viscosities were measured on a TA Instrument Model CSL 500 Cari-Med Rheometer. A cone and plate method with a 2 cm, 1 degree geometry was used.

Thermal Measurements

Char yields at 600° C. were measured from a thermo-gravimetric analysis run on a TA Instrument Model Number 2050 Thermal Gravimetric Analyzer (TGA). The thermo-gravimetric analysis was under nitrogen to 600° C. at 10° C. per minute. The temperature at 5 percent weight loss was also measured from the thermo-gravimetric analysis.

Example 1(a)

Bis A/Furfurylamine Benzoxazine-Furan Compound

To begin, about 260 grams of dioxane (Aldrich Chemical Co., Milwaukee, Wis.), about 2.1 moles of paraformaldehyde (Aldrich Chemical Co., Milwaukee, Wis.), about 1 mole of furfurylamine (Aldrich Chemical Co., Milwaukee, Wis.), and about 0.5 mole of bisphenol A "Bis A" (PARABIS, The Dow Chemical Company, Midland, Mich.) were combined in a reaction flask fitted with a mechanical stirrer, condenser and thermometer. Then, additional dioxane (about 150 grams) was added to wash all of the reactants to the bottom of the reactor. The mixture was then heated to 90° C. and maintained at this temperature for about 25 hours. The homogeneous mixture was then cooled to room temperature and the solvent removed at reduced pressure on a rotary evaporator. The final solvent stripping was done at about 1 mbar at 125° C. until no more bubbling was observed. The product was poured into a glass dish containing an aluminum foil insert and allowed to cool to room temperature.

Example 1(b)

Bis A/Furfurylamine Polybenzoxazine

The benzoxazine-furan compound of Example 1(a) was sealed in a glass bottle, then heated in an oven as follows. The sealed bottle containing the compound was placed in an oven maintained at 150° C., which was then heated to 210° C. at 1° C. per minute. The sample was maintained at 210° C. for about 3 hours to form a polybenzoxazine.

The polybenzoxazine had a char yield of 56 percent and a 5 percent loss temperature of 355° C., which is also shown in Table 1.

Examples 2–4

Bis A/Furfurylamine-Furoin Polybenzoxazine

Polybenzoxazines of the benzoxazine-furan compound of Example 1(a) and furoin, a furan compound, (Aldrich Chemical Co., Milwaukee, Wis.) were prepared by mixing them for about 15 seconds using a WIG-L BUG mixer (Wilmad Glass Co., Buena, N.J.). Each mixture was then cured by the same method of Example 1(b). The amount of each component, furan rings/benzoxazine ring ratio, char yield and the loss temperature are shown for each of these Examples in Table 1.

Examples 5–7

Bis A/Furfurylamine-Furil Polybenzoxazine

Polybenzoxazines of the benzoxazine-furan compound of Example 1(a) and furil, a furan compound, (Aldrich Chemical Co., Milwaukee, Wis.) were prepared by mixing them for about 15 seconds using a WIG-L BUG mixer. Each mixture was then cured by the same method of Example 1(b). The amount of each component, furan rings/benzoxazine ring ratio, char yield and the loss temperature are shown for each of these Examples in Table 1.

Comparative Example 1(a)

Bis A/Aniline Benzoxazine Compound

To begin, about 260 grams of dioxane (Aldrich Chemical Co., Milwaukee, Wis.), about 2.1 moles of paraformaldehyde (Aldrich Chemical Co., Milwaukee, Wis.), about 1 mole of aniline (Aldrich Chemical Co., Milwaukee, Wis.), and about 0.5 mole of bisphenol A (PARABIS, The Dow Chemical Company, Midland Mich.) were combined in a reaction flask fitted with a mechanical stirrer, condenser and thermometer. Then, additional dioxane (about 150 grams)

was added to wash all of the reactants to the bottom of the reactor. The mixture was then heated to 90° C. and maintained at this temperature for about 25 hours. The homogeneous mixture was then cooled to room temperature and the solvent removed at reduced pressure on a rotary evaporator. The final solvent stripping was done at about 1 mbar at 125° C. until no more bubbling was observed. The product was poured into a glass dish containing an aluminum foil insert and allowed to cool to room temperature.

Comparative Example 1(b)

Bis A/Aniline Polybenzoxazine

The benzoxazine monomer of Comparative Example 1(a) was sealed in a glass bottle, then heated in an oven as follows. The sealed bottle containing the monomer was placed in an oven maintained at 150° C., which was then heated to 210° C. at 1° C. per minute. The sample was maintained at 210° C. for about 3 hours to form a polybenzoxazine.

The polybenzoxazine had a char yield of 32 percent and a 5 percent loss temperature of 329° C., which is also shown in Table 1.

Examples 8–10

Bis A/Aniline-Bis A/Furfurylamine Polybenzoxazine

Polybenzoxazines of the benzoxazine-furan compound of Example 1(a) and benzoxazine compound of Comparative Example 1(a) were prepared as follows. The components were first mixed by placing the desired amounts of each in a pan and then adding a sufficient amount of tetrahydrofuran (THF), while agitating, to dissolve all of the components. Once all of the components had been dissolved, the THF was removed by first warming slightly and then applying a vacuum at about 90° C. to 100° C. until no bubbling was observed. The mixtures, after removing the THF, were checked by gas chromatography to ensure no residual solvent remained. The mixture was then cured in the same manner as described by Example 1(b) to form a polybenzoxazine. The amount of each component, furan rings/benzoxazine ring ratio, char yield and the loss temperature is shown for each of these Examples in Table 1.

Examples 11–13

Bis A/Aniline-Furoin Polybenzoxazine

Polybenzoxazines of the benzoxazine of Comparative Example 1(a) and furoin were prepared by the same method described by Examples 2–4. The amount of each component, furan rings/benzoxazine ring ratio, char yield and the loss temperature is shown for each of these Examples in Table 1.

Examples 14–16

Bis A/Aniline-Furil Polybenzoxazine

Polybenzoxazines of the benzoxazine of Comparative Example 1(a) and furil were prepared by the same method described by Examples 5–7. The amount of each component, furan rings/benzoxazine ring ratio, char yield and the loss temperature is shown for each of these Examples in Table 1.

From the results shown in Table 1, it is readily apparent that the char yield increases substantially with increasing furan ring/benzoxazine ring ratio. Also, the increase in char yield does not significantly change the 5 percent loss temperature. The improved char yield is clearly exemplified by comparing Example 1(b) to Comparative Example 1(b). These polybenzoxazines are made from a starting benzoxazine monomer with the same structure, except that Example 1(b) has a furan pendant off each benzoxazine ring (i.e., benzoxazine-furan compound compared to benzoxazine-aniline compound, respectively). The results show that the furan ring presence results in almost doubling the char yield and an increase in 5 percent loss temperature of Example 1(b) compared to Comparative Example 1(b).

The results of Table 1 also show that the inclusion of a furan compound (e.g., furil or furoin) also improves the char yield of a polybenzoxazine of a benzoxazine compound (see Examples 11–14). The results also show that a furan compound improves the char yield of a polybenzoxazine of a benzoxazine-furan compound (see Examples 2–7).

TABLE 1

| Example | Pre-Cure Polybenzoxazine Composition | Furan/ Benzoxazine Ring Ratio | 5 Wt % Loss Temperature (° C.) | % Char Yield |
|---|---|---|---|---|
| 1(b) | 100 wt % BisA/FA | 1.0 | 355 | 56 |
| 2 | 90 wt % Bis A/FA & 10 wt % furoin | 1.27 | 348 | 59 |
| 3 | 80 wt % Bis A/FA & 20 wt % furoin | 1.61 | 347 | 63 |
| 4 | 60 wt % Bis A/FA & 40 wt % furoin | 2.63 | 344 | 73 |
| 5 | 90 wt % Bis A/FA & 10 wt % furil | 1.27 | 353 | 61 |
| 6 | 80 wt % Bis A/FA & 20 wt % furil | 1.62 | 358 | 64 |
| 7 | 60 wt % Bis A/FA & 40 wt % furil | 2.65 | 350 | 70 |
| 8 | 25 wt % Bis A/FA & 75 wt % Bis A/aniline | 0.25 | 336 | 40 |
| 9 | 50 wt % Bis A/FA & 50 wt % Bis A/aniline | 0.50 | 347 | 47 |
| 10 | 75 wt % Bis A/FA & 25 wt % Bis A/aniline | 0.75 | 342 | 51 |
| 11 | 90 wt % Bis A/aniline & 10 wt % furoin | 0.27 | 315 | 43 |
| 12 | 80 wt % Bis A/aniline & 20 wt % furoin | 0.60 | 327 | 52 |
| 13 | 60 wt % Bis A/aniline & 40 wt % furoin | 1.60 | 335 | 64 |
| 14 | 90 wt % Bis A/aniline & 10 wt % furil | 0.27 | 329 | 42 |
| 15 | 80 wt % Bis A/aniline & 20 wt % furil | 0.61 | 339 | 54 |
| 16 | 60 wt % Bis A/aniline & 40 wt % furil | 1.62 | 330 | 67 |
| Comp. Example 1(b) | 100 wt % Bis A/aniline | 0 | 329 | 32 |

Bis A = bisphenol A
FA = furfurylamine

Examples 17–19

Bis A/Aniline- Dimethyl 3,4-Furandicarboxylate (DMFDC) Polybenzoxazine

Polybenzoxazines of the benzoxazine compound of Comparative Example 1(a) and DMFDC (Aldrich Chemical Co., Milwaukee, Wis.) were prepared by weighing out the desired amount of each into a common container and then melting the components by heating to less than 100° C. to form a homogeneous liquid. This mixture was then cured by the same method described by Example 1(b) to form a polybenzoxazine. The amount of each component, furan rings/benzoxazine ring ratio, char yield and the loss temperature is shown for each of these Examples in Table 2.

Examples 20 & 21

Bis A/Furfurylamine- DMFDC Polybenzoxazine

Polybenzoxazines of the benzoxazine-furan compound of Example 1(a) and DMFDC (Aldrich Chemical Co., Milwaukee, Wis.) were prepared by weighing out the desired amount of each into a common container and then melting the components by heating to less than 100° C. to form a homogeneous liquid. This mixture was then cured by the same method described by Example 1(b) to form a polybenzoxazine. The amount of each component, furan rings/benzoxazine ring ratio, char yield and the loss temperature is shown for each of these Examples in Table 2.

The results in Table 2 show that even a furan compound with only one furan ring and no other reactive group will improve the char yield of a polybenzoxazine of a benzoxazine compound (see Examples 17–19 and Comparative Example 1 of Table 1). This is so even though DMFDC, when cured by itself using the same method described herein, has a char yield of zero (nothing remained after 180° C.) a 5 percent loss temperature of 111° C. The results in Table 2 also show that the DMFDC may not be as effective when mixed with a benzoxazine-furan compound (see Examples 20 and 21 and Example 1 of Table 1). That is to say, the DMFDC appears to have reduced the char yield of the polybenzoxazine of Bis A/furfurylamine.

TABLE 2

| Example | Pre-Cure Polybenzoxazine Composition | Furan/ Benzoxazine Ring Ratio | 5 Wt % Loss Temperature (° C.) | % Char Yield |
|---|---|---|---|---|
| 17 | 90 wt % Bis A/aniline & 10 wt % DMFDC | 0.14 | 331 | 39 |
| 18 | 80 wt % Bis A/aniline & 20 wt % DMFDC | 0.31 | 313 | 41 |
| 19 | 60 wt % Bis A/aniline & 40 wt % DMFDC | 0.84 | 273 | 42 |
| 20 | 80 wt % Bis A/FA & 20 wt % DMFDC | 1.32 | 311 | 53 |
| 21 | 60 wt % Bis A/FA & 40 wt % DMFDC | 1.85 | 291 | 45 |

Bis A = bisphenol A
FA = furfurylamine
DMFDC = dimethyl 3,4-furandicarboxylate

Example 22

Bis A/Furfurylamine-4-t-Butylphenol (TBP)/ Furfurylamine Polybenzoxazine

70 Parts by weight of Bis A/furfurylamine of Example 1(a) were mixed with 30 parts by weight of a benzoxazine-furan compound of TBP/furfurylamine. The TBP/furfurylamine was made using the same method described by Example 1(a). The TBP was obtained from Aldrich Chemical, described previously. The viscosity of the mixture at various temperatures was determined. The char yield and 5 percent loss temperature of the polybenzoxazine of this mixture was also determined. The curing method used to form the polybenzoxazine was the same as described by Example 1(b). The results are shown in Table 3.

Example 23

Bis A/Furfurylamine-2,4-Dimethylphenol (DMP)/ Furfurylamine Polybenzoxazine

70 Parts by weight of Bis A/furfurylamine of Example 1(a) was mixed with 30 parts by weight of a benzoxazine-furan compound of 2,4-dimethylphenol (DMP)/ furfurylamine. The DMP/furfurylamine was made using the same method described by Example 1(a). The DMP was obtained from Aldrich Chemical, described previously. The viscosity of the mixture at various temperatures was determined. The char yield and 5 percent loss temperature of the polybenzoxazine of this mixture was also determined. The curing method used to form the polybenzoxazine was the same as described by Example 1(b). The results are shown in Table 3.

Example 24

Bisphenol F (Bis F)/Furfurylamine Polybenzoxazine

A benzoxazine-furan compound and polybenzoxazine made therefrom were made by the same methods described in Example 1 (a and b), except that the phenol was Bisphenol F (Mitsui Toatsu Toyko, Japan) instead of Bis A. The viscosity of the benzoxazine-furan compound prior to curing and the char yield and 5 percent loss temperature of the polybenzoxazine are shown in Table 3.

Example 25

(Bis F)/Furfurylamine-TBP/Furfurylamine Polybenzoxazine

70 Parts by weight of Bis F/furfurylamine of Example 24 were mixed with 30 parts by weight of a benzoxazine-furan compound of TBP/furfurylamine. The TBP/furfurylamine was made by the same method described in Example 22. The curing method used to form the polybenzoxazine was the same as described by Example 1(b). The viscosity of the mixture, prior to curing, the char yield and 5 percent loss temperature of the polybenzoxazine are shown in Table 3.

Example 26

(Bis F)/Furfurylamine-DMP/Furfurylamine Polybenzoxazine

70 Parts by weight of Bis F/furfurylamine of Example 24 were mixed with 30 parts by weight of a benzoxazine-furan compound of dimethylphenol (DMP)/furfurylamine. The DMP/furfurylamine was made using the same method described by Example 23. The curing method used to form the polybenzoxazine was the same as described by Example 1(b). The viscosity of the mixture, prior to curing, the char yield and 5 percent loss temperature of the polybenzoxazine are shown in Table 3.

Example 27

Biphenol/Furfurylamine Polybenzoxazine

A benzoxazine-furan compound and polybenzoxazine made therefrom were made by the same methods described in Example 1 (a and b), except that the phenol was 2,2'-Biphenol (Aldrich Chemical Company) instead of Bis A. The viscosity of the benzoxazine-furan compound, prior to curing, the char yield and 5 percent loss temperature of the polybenzoxazine are shown in Table 3.

Example 28

Biphenol/Furfurylamine-TBP/Furfurylamine Polybenzoxazine

70 Parts by weight of biphenol/furfurylamine of Example 27 was mixed with 30 parts by weight of a benzoxazine-furan compound of TBP/furfurylamine. The TBP/furfurylamine was made by the same method described in Example 22. The curing method used to form the polybenzoxazine was the same as described by Example 1(b). The viscosity of the mixture, prior to curing, the char yield and 5 percent loss temperature of the polybenzoxazine are shown in Table 3.

Example 29

Biphenol/Furfurylamine-DMP/Furfurylamine Polybenzoxazine

70 Parts by weight of biphenol/furfurylamine of Example 27 was mixed with 30 parts by weight of a benzoxazine-furan compound of DMP/furfurylamine. The DBP/furfurylamine was made by the same method described in Example 23. The curing method used to form the polybenzoxazine was the same as described by Example 1(b). The viscosity of the mixture, prior to curing, the char yield and 5 percent loss temperature of the polybenzoxazine are shown in Table 3.

Comparative Example 2

Bisphenol F (Bis F)/Aniline Polybenzoxazine

A benzoxazine compound and polybenzoxazine made therefrom were made by the same methods described in Comparative Example 1 (a and b), except that the phenol was Bisphenol F (Aldrich Chemical Company) instead of Bis A. The viscosity of the benzoxazine compound, prior to curing, the char yield and 5 percent loss temperature of the polybenzoxazine are shown in Table 3.

Comparative Example 3

Biphenol/Aniline Polybenzoxazine

A benzoxazine compound and polybenzoxazine made therefrom were made by the same methods described in Comparative Example 1 (a and b), except that the phenol was 2,2-Biphenol (Aldrich Chemical Company) instead of Bis A. The viscosity of the benzoxazine compound, prior to curing, the char yield and 5 percent loss temperature of the polybenzoxazine are shown in Table 3.

From Table 3, it is readily apparent that the polybenzoxazine of a benzoxazine-furan compound (Examples 24 and 27) have substantially increased 5 percent loss temperature compared to a polybenzoxazine of a benzoxazine having the same structure, except for the absence of a furan group (Comparative Examples 2 and 3).

Further, the results shown in Table 3 show that the use of benzoxazine-furan compound containing only 1 benzoxazine ring and one furan ring reduces the viscosity of the benzoxazine mixture of a benzoxazine-furan compound containing two benzoxazine and furan rings (see Examples 22, 23, 25, 26, 28 and 29). However, this reduced viscosity does not result in a substantial (i.e., hardly any) reduction in char yield or 5 percent loss temperature, while the viscosity is reduced by an order of magnitude (see previously described examples compared to Examples 1, 24 and 27).

TABLE 3

| Example | Pre-Cure Polybenzoxazine Composition | Viscosity @ 100° C. (cps) | Viscosity @ 120° C. (cps) | Viscosity @ 140° C. (cps) | Viscosity @ 160° C. (cps) | Furan/ Benzoxazine Ring Ratio. | 5 Wt % Loss Temperature (° C.) | % Char Yield |
|---|---|---|---|---|---|---|---|---|
| 1 (a and b) | 100 wt % Bis A/FA | ND | 14500 | 1708 | 372 | 2.0 | 355 | 56 |
| 22 | 70 wt % Bis A/FA & 30 wt % TBP/FA | 8956 | 622 | 142 | 83 | 1.0 | 331 | 51 |
| 23 | 70 wt % Bis A/FA & 30 wt % DMP/FA | 805 | 207 | 83 | 45 | 1.0 | 332 | 51 |
| 24 | 100 wt % Bis F/FA | 4683 | 1000 | 257 | 100 | 1.0 | 366 | 64 |
| 25 | 70 wt % Bis F/FA & 30 wt % TBP/FA | 2171 | 255 | 83 | <100 | 1.0 | 362 | 59 |
| 26 | 70 wt % Bis F/FA & 30 wt % DMP/FA | 273 | 86 | 35 | <100 | 1.0 | 354 | 60 |
| 27 | 100 wt % biphenol/FA | ~350000 | 25560 | 3573 | 1433 | 1.0 | 366 | 73 |
| 28 | 70 wt % biphenol/FA & 30 wt % TBP/FA | 13780 | 1117 | 299 | 141 | 1.0 | 362 | 66 |
| 29 | 70 wt % biphenol/FA & 30 wt % DMP/FA | 2122 | 386 | 135 | <100 | 1.0 | 354 | 66 |
| Comp. Ex. 2 | 100 wt % Bis F/aniline | 3463 | 210 | <100 | <100 | 0 | 344 | 48 |
| Comp. Ex. 3 | 100 wt % biphenol/aniline | ND | >58600 | 4865 | 387 | 0 | 304 | 45 |

What is claimed is:

1. A method to make a high char yield polybenzoxazine comprising, forming a mixture having
(i) a benzoxazine compound of the formula

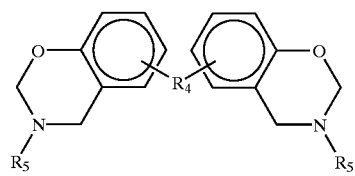

where $R_4$ is (a) a divalent radical that is aliphatic, aromatic or combination thereof that contains from 1 to 35 carbon atoms with up to 5 atoms selected from oxygen, nitrogen, sulfur, phosphorous, halogen or combinations thereof; (b) a single bond or (c) S, $S_2$, SO, $SO_2$, O or CO and $R_5$ is H, unsubstituted alkyl having one to 24 carbon atoms, an unsubstituted aryl having 6 to 24 carbon atoms, or $R_5$ has a formula selected from the group consisting of:

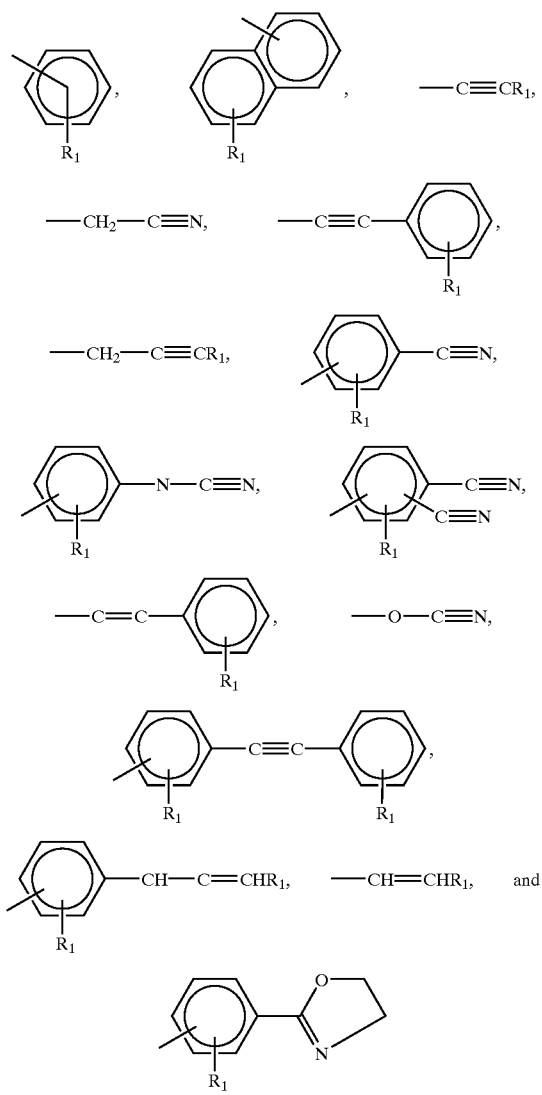

where X is

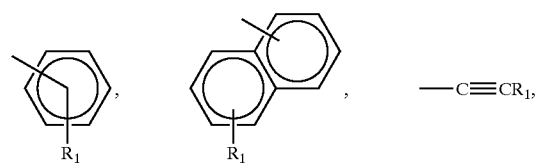

where $R_1$ is H, OH or an unsubstituted alkyl of 1 to 6 carbons;

(ii) a furan compound selected from the group consisting of furan, furfural, furoin, furfuryl alcohol, furil, dimethyl 3,4-furandicarboxylate, a furan having a formula selected from the group consisting of,

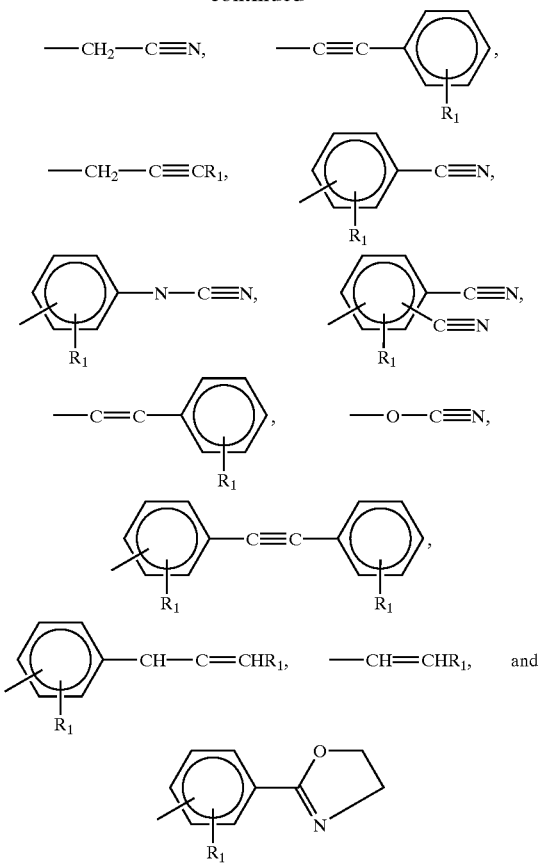

and a furan having the formula,

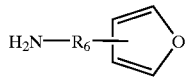

where $R_6$ is a single bond or a 1 to 5 carbon alkylene;

(iii) a benzoxazine-furan compound having a formula of,

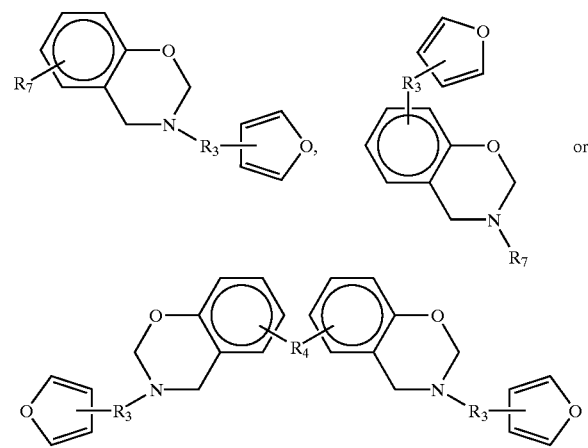

where $R_3$ is a single bond or an alkylene having one to 6 carbon atoms and $R_7$ is H or unsubstituted alkyl having from 1–6 carbon atoms; or (iv) combinations thereof, such that the mixture has a furan ring to benzoxazine ring ratio of about 0.001 to about 10 and heating the mixture for a sufficient time to form the polybenzoxazine.

2. The method of claim 1 wherein the furan ring to benzoxazine ring ratio is at least 0.01.

3. The method of claim 2 wherein the ratio is at least 0.1.

4. The method of claim 3 wherein the ratio is at most 4.

5. The method of claim 1 wherein $R_5$ is phenyl.

6. The method of claim 5 wherein $R_4$ is a single carbon that has bonded to it one or more groups selected from H, $CH_3$, $C_2H_5$, $C_3H_7$, $n-C_3H_7$, $i-C_3H_7$, cyclohexyl, bicyclohexyl(2.2.1)heptyl, phenyl, $CF_2$, $CF_3$, $CCl_3$, $CF_2Cl$, CN, $(CH_2)_2COOH_3$ and $PO(OCH_3)_2$.

7. The method of claim 6 wherein $R_4$ is a carbon directly bonded to two methyl groups.

8. The method of claim 1 wherein the furan compound is furan, furil, furoin, furfuryl alcohol, furfural, furfurylamine or methylfurfurylamine.

9. The method of claim 8 wherein the furan compound is furil, furoin, furfural, furfirylamine or methylfurfurylamine.

10. The method of claim 1 wherein the mixture is heated to a temperature of at least 100° C.

11. A polybenzoxazine made by the method of claim 1.

12. A method to make high char yield polybenzoxazine comprising forming a mixture having (i) a benzoxazine compound having the formula

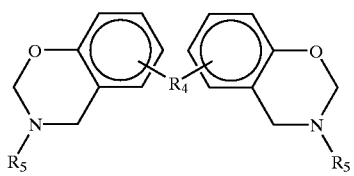

where $R_4$ is (a) a divalent radical that is aliphatic, aromatic or combination thereof that contains from 1 to 35 carbon atoms with up to 5 atoms selected from oxygen, nitrogen, sulfur, phosphorous, halogen or combinations thereof; (b) a single bond or (c) S, $S_2$, SO, $SO_2$, O or CO and $R_5$ is H, unsubstituted alkyl having one to 24 carbon atoms, an unsubstituted aryl having 6 to 24 carbon atoms, or $R_5$ has a formula selected from the group consisting of:

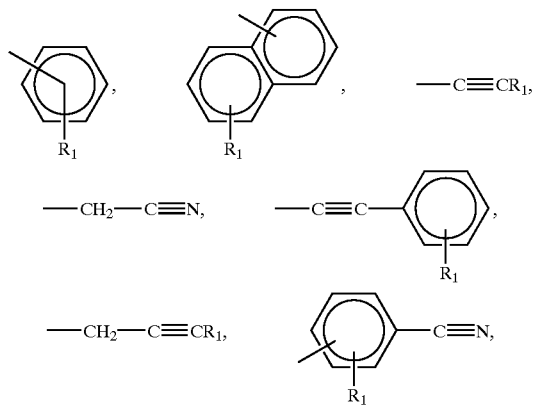

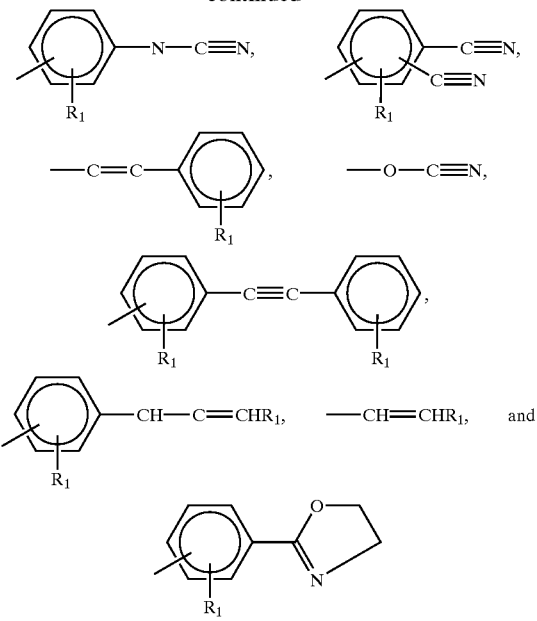

where $R_1$ is H, OH or an unsubstituted alkyl of 1 to 6 carbons and (ii) a benzoxazine-furan compound having a formula selected from the group consisting of:

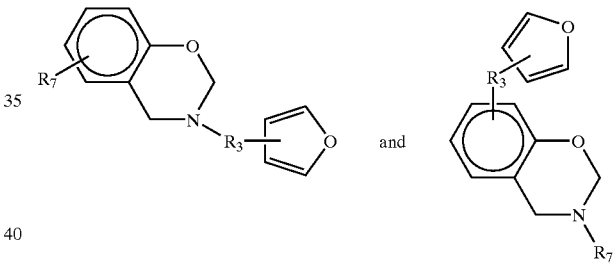

where $R_3$ is a singe bond or an unsubstituted alkylene having one to 6 carbon atoms and $R_7$ is H or an unsubstituted alkyl having from 1 to 6 carbon atoms, such that the mixture has a furan to ring ratio to benzoxazine ratio of about 0.001 to about 10 and heating the mixture for a time sufficient to form the polybenzoxazine.

13. The method of claim 12 wherein $R_4$ is a single carbon that has bonded to it one or more groups selected from the group consisting of H, $CH_3$, $C_2H_5$, $C_3H_7$, $n-C_3H_7$, $i-C_3H_7$, cyclohexyl, bicyclohexyl(2.2.1)heptyl, phenyl, $CF_2$, $CF_3$, $CCl_3$, $CF_2Cl$, CN, $(CH_2)_2COOH_3$ and $PO(OCH_3)_2$.

14. The method of claim 13 wherein $R_4$ is a carbon directly bonded to two methyl groups.

15. The method of claim 13 wherein $R_5$ is H, an unsubstituted alkyl having one to 24 carbon atoms or an unsubstituted aryl having 6 to 24 carbon atoms.

16. The method of claim 12 wherein the mixture is heated to a temperature of at least 100° C.

17. A polybenzoxazine made by the method of claim 12.

18. A polybenzoxazine made by the method of claim 15.

19. A method of making a high char yield polybenzoxazine comprising, forming a mixture having a benzoxazine-furan compound that has a formula of,

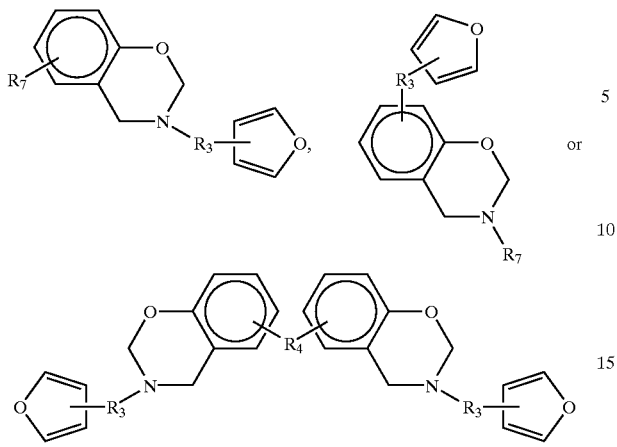

where $R_3$ is a single bond or an unsubstituted alkylene having one to 6 carbon atoms, $R_4$ is (a) a divalent radical that is aliphatic, aromatic or combination thereof that contains from 1 to 35 carbon atoms with up to 5 atoms selected from oxygen, nitrogen, sulfur, phosphorous, halogen or combinations thereof; (b) a single bond or (c) S, $S_2$, SO, $SO_2$, O or CO and $R_7$ is H or an unsubstituted alkyl having from 1 to 6 carbon atoms and heating the mixture for a time sufficient to form the polybenzoxazine.

20. The method of claim 19 wherein $R_4$ is a single carbon that has bonded to it one or more groups selected from H, $CH_3$, $C_2H_5$, $C_3H_7$, n-$C_3H_7$, i-$C_3H_7$, cyclohexyl, bicyclohexyl(2.2.1)heptyl, phenyl, $CF_2$, $CF_3$, $CCl_3$, $CF_2Cl$, CN, $(CH_2)_2COOH_3$ and $PO(OCH_3)_2$.

21. The method of claim 20 wherein $R_4$ is a carbon directly bonded to two methyl groups.

22. The method of claim 19 wherein $R_4$ the mixture is heated to a temperature of at least 100° C.

23. A polybenzoxazine made by the method of claim 19.

24. A method of making a high char yield polybenzoxazine comprising, forming a mixture having
(i) a benzoxazine compound of the formula

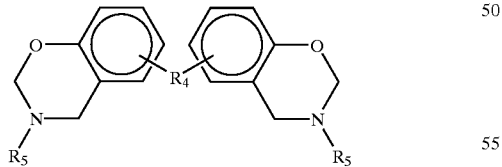

where $R_4$ is (a) a divalent radical that is aliphatic, aromatic or combination thereof that contains from 1 to 35 carbon atoms with up to 5 atoms selected from oxygen, nitrogen, sulfur, phosphorous, halogen or combinations thereof; (b) a single bond or (c) S, $S_2$, SO, $SO_2$, O or CO and $R_5$ is H, unsubstituted alkyl having one to 24 carbon atoms, an unsubstituted aryl having 6 to 24 carbon atoms, or $R_5$ has a formula selected from the group consisting of:

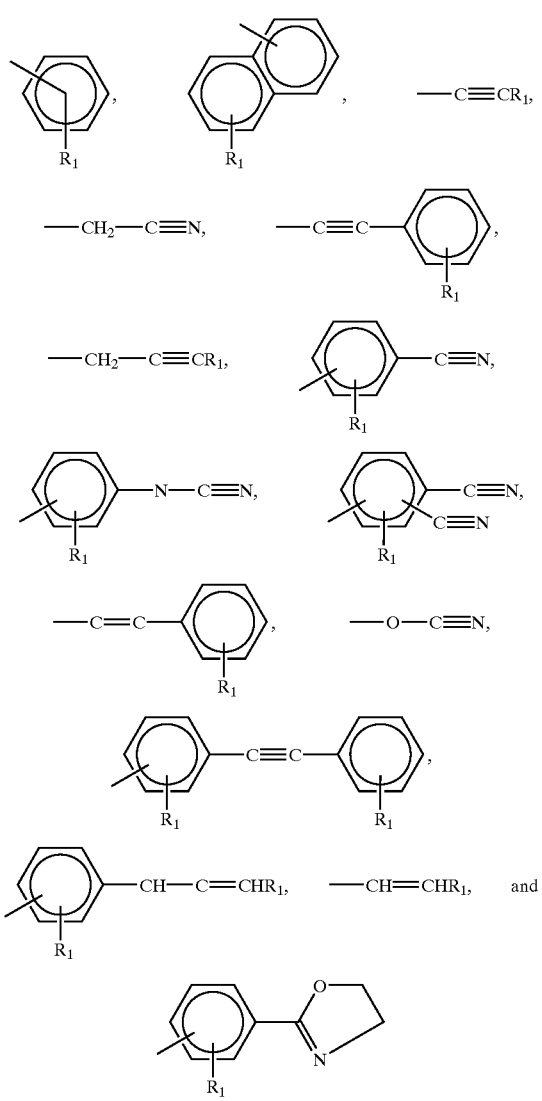

where $R_1$ is H, OH or an unsubstituted alkyl of 1 to 6 carbons and (ii) a furan compound selected from the group consisting of furan, furfural, furoin, furfuryl alcohol, furil, dimethyl 3,4-furandicarboxylate, a furan having a formula selected from the group consisting of,

where X is

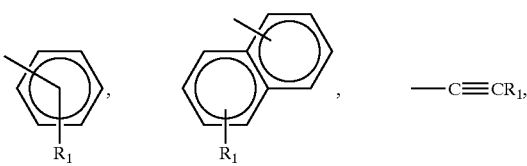

23
-continued

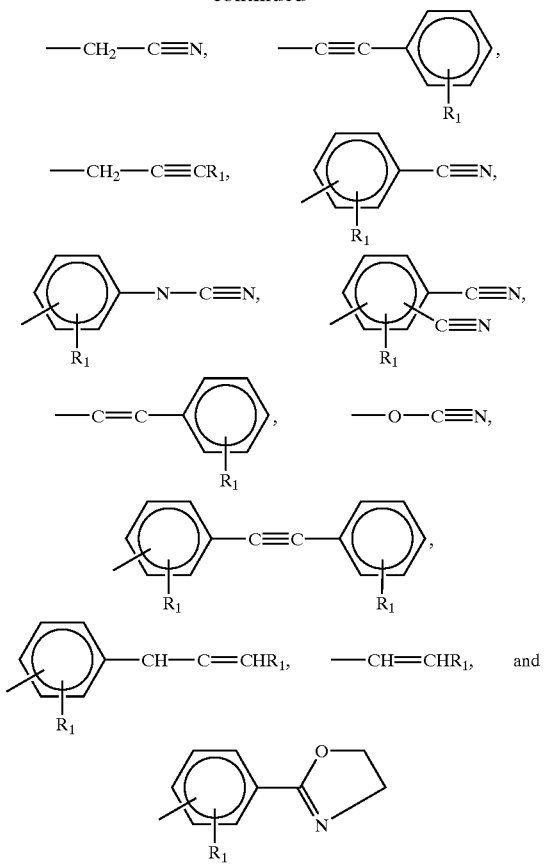

and a furan having the formula,

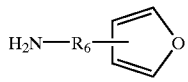

where $R_6$ is a single bond or a 1 to 5 carbon alkylene such that the mixture has a furan ring to benzoxazine ring ratio from about 0.001 to about 10 and heating the mixture for a sufficient time to form the polybenzoxazine.

25. The method of claim 24 wherein the furan ring to benzoxazine ring ratio is at least 0.01.

26. The method of claim 25 wherein the ratio is at least 0.1.

27. The method of claim 26 wherein the ratio is at most 4.

28. The method of claim 24 wherein $R_5$ is phenyl.

29. The method of claim 24 wherein $R_4$ is a single carbon that has bonded to it one or more groups selected from H, $CH_3$, $C_2H_5$, $C_3H_7$, n-$C_3H_7$, i-$C_3H_7$, cyclohexyl, bicyclohexyl(2.2.1)heptyl, phenyl, $CF_2$, $CF_3$, $CCl_3$, $CF_2Cl$, CN, $(CH_2)_2COOH_3$ and $PO(OCH_3)_2$.

24

30. The method of claim 29 wherein $R_4$ is a carbon directly bonded to two methyl groups.

31. The method of claim 24 wherein the furan compound is furan, furil, furoin, furfuryl alchol, furfural, furfurylamine or methylfurfurylamine.

32. The method of claim 31 wherein the furan compound is furil, furoin, furfural, furfurylamine or methylfurfurylamine.

33. The method of claim 24 wherein the mixture is heated to a temperature of at least 100° C.

34. A polybenzoxazine made by the method of claim 24.

35. A mixture useful for preparing a polybenzoxazine comprised of (i) a benzoxazine compound that does not contain a furan group, (ii) a furan compound that does not contain a benzoxazine group, (iii) a benzoxazine-furan compound or (iv) combinations thereof, wherein the mixture has a furan ring to benzoxazine ring ratio of about 0.001 to about 10.

36. A benzoxazine monomer useful for preparing high char yield polybenzoxazines, the benzoxazine monomer having the formula:

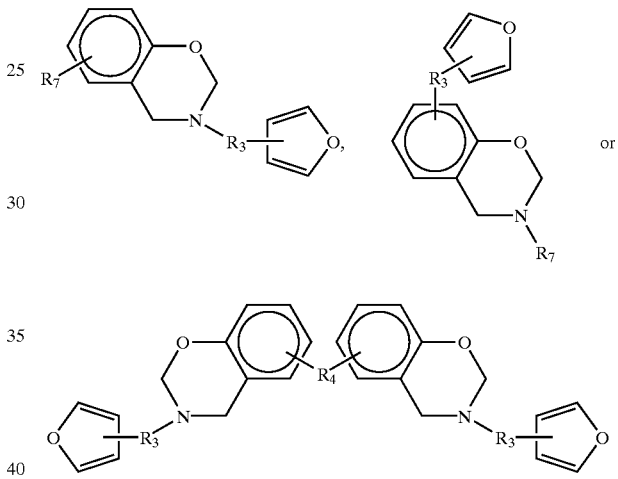

where $R_3$ is a single bond or an unsubstituted alkylene having one to 6 carbon atoms, $R_4$ is (a) a divalent radical that is aliphatic, aromatic or combination thereof that contains from 1 to 35 carbon atoms with up to 5 atoms selected from oxygen, nitrogen, sulfur, phosphorous, halogen or combinations thereof; (b) a single bond or (c) S, $S_2$, SO, $SO_2$, O or CO and $R_7$ is H or an unsubstituted alkyl having from 1 to 6 carbon atoms.

37. The monomer of claim 36 wherein $R_4$ is a single carbon that has bonded to it one or more groups selected from H, $CH_3$, $C_2H_5$, $C_3H_7$, n-$C_3H_7$, i-$C_3H_7$, cyclohexyl, bicyclohexyl(2.2.1)heptyl, phenyl, $CF_2$, $CF_3$, $CCl_3$, $CF_2Cl$, CN, $(CH_2)_2COOH_3$ and $PO(OCH_3)_2$.

38. The monomer of claim 37 wherein $R_4$ is a carbon directly bonded to two methyl groups.

* * * * *